(12) United States Patent
Tsunoda et al.

(10) Patent No.: US 10,711,047 B2
(45) Date of Patent: Jul. 14, 2020

(54) CDCA1 EPITOPE PEPTIDES AND VACCINES CONTAINING THE SAME

(71) Applicant: ONCOTHERAPY SCIENCE, INC., Kanagawa (JP)

(72) Inventors: Takuya Tsunoda, Kanagawa (JP); Ryuji Ohsawa, Kanagawa (JP); Sachiko Yoshimura, Kanagawa (JP)

(73) Assignee: ONCOTHERAPY SCIENCE, INC., Kawasaki-shi, Kanagawa (JP)

( * ) Notice: Subject to any disclaimer, the term of this patent is extended or adjusted under 35 U.S.C. 154(b) by 670 days.

(21) Appl. No.: 15/176,444

(22) Filed: Jun. 8, 2016

(65) Prior Publication Data

US 2016/0272692 A1    Sep. 22, 2016

Related U.S. Application Data

(62) Division of application No. 12/999,051, filed as application No. PCT/JP2009/002771 on Jun. 18, 2009, now Pat. No. 9,387,238.

(60) Provisional application No. 61/074,062, filed on Jun. 19, 2008, provisional application No. 61/197,599, filed on Oct. 28, 2008.

(51) Int. Cl.
| | |
|---|---|
| A61K 39/00 | (2006.01) |
| C07K 14/47 | (2006.01) |
| C12N 5/0783 | (2010.01) |
| C07K 7/06 | (2006.01) |
| A61K 38/00 | (2006.01) |

(52) U.S. Cl.
CPC ...... *C07K 14/4748* (2013.01); *A61K 39/0011* (2013.01); *C07K 14/47* (2013.01); *C12N 5/0638* (2013.01); *A61K 38/00* (2013.01); *A61K 39/00* (2013.01); *A61K 2039/5154* (2013.01); *A61K 2039/53* (2013.01); *A61K 2039/572* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 6,699,703 B1 | 3/2004 | Doucette-Stamm et al. | |
| 6,858,204 B2 | 2/2005 | Henderson et al. | |
| 6,867,283 B2 | 3/2005 | Barnea et al. | |
| 7,214,786 B2 | 5/2007 | Kovalic et al. | |
| 7,531,300 B2 | 5/2009 | Nakamura et al. | |
| 7,776,341 B2 | 8/2010 | Belisle et al. | |
| 7,943,295 B2 | 5/2011 | Nakamura et al. | |
| 7,998,695 B2 | 8/2011 | Nakamura et al. | |
| 8,455,444 B2 | 6/2013 | Nishimura et al. | |
| 8,598,125 B2 * | 12/2013 | Nishimura | A61K 39/0011 514/19.2 |
| 9,687,538 B2 * | 6/2017 | Nishimura | A61K 39/0011 |

| | | |
|---|---|---|
| 2002/0172952 A1 | 11/2002 | Henderson et al. |
| 2006/0024692 A1 | 2/2006 | Nakamura et al. |
| 2006/0088527 A1 | 4/2006 | Henderson et al. |
| 2006/0216301 A1 | 9/2006 | Tahara et al. |
| 2007/0053922 A1 | 3/2007 | Sette et al. |
| 2009/0175844 A1 | 7/2009 | Nakamura et al. |
| 2009/0208514 A1 | 8/2009 | Nakamura et al. |
| 2009/0215683 A1 | 8/2009 | Nakamura et al. |
| 2009/0286856 A1 | 11/2009 | Nakamura et al. |
| 2009/0317392 A1 | 12/2009 | Nakamura et al. |
| 2011/0152199 A1 | 6/2011 | Nishimura et al. |

(Continued)

FOREIGN PATENT DOCUMENTS

| | | |
|---|---|---|
| CN | 1357006 A | 7/2002 |
| CN | 101835892 A | 9/2010 |

(Continued)

OTHER PUBLICATIONS

Celis et al (Mol. Innnnunol. 1994, 31(18): 1423-1430) (Year: 1994).*
Karin et al (J. Exp. Med., 1994, 180, 2227-2237) (Year: 1994).*
Berger et al (Int. J. Cancer. 111: 229-237, 2004) (Year: 2004).*
Marchand et al (Int. J. Cancer 80: 219-230, 1999) (Year: 1999).*
Marchand et al (Exp. Opin. Biol. Ther. 1(3): 497-510, 2001) (Year: 2001).*

(Continued)

*Primary Examiner* — G. R. Ewoldt
*Assistant Examiner* — Marianne DiBrino
(74) *Attorney, Agent, or Firm* — Kilpatrick Townsend & Stockton LLP

(57) ABSTRACT

Peptide vaccines against cancer are described herein. In particular, the present invention describes epitope peptides derived from CDCA1 that elicit CTLs. The present invention also provides established CTLs that specifically recognize HLA-A24 positive target cells pulsed with the peptides. Antigen-presenting cells and exosomes that present any of the peptides, as well as methods for inducing antigen-presenting cells are also provided. The present invention further provides pharmaceutical agents containing the CDCA1 polypeptides or polynucleotides encoding thereof, as well as exosomes and antigen-presenting cells as active ingredients. Furthermore, the present invention provides methods for treating and/or prophylaxis of (i.e., preventing) cancers (tumors), and/or prevention of postoperative recurrence thereof, as well as methods for inducing CTLs, methods for inducing anti-tumor immunity, using the CDCA1 polypeptides, polynucleotides encoding the polypeptides, exosomes or antigen-presenting cells presenting the polypeptides, or the pharmaceutical agents of the present invention. The cancers to be targeted include, but are not limited to, breast cancer, bladder cancer, esophageal cancer, small cell lung cancer (SCLC) and non-small cell lung cancer (NSCLC).

1 Claim, 3 Drawing Sheets
Specification includes a Sequence Listing.

(56) References Cited

U.S. PATENT DOCUMENTS

| | | |
|---|---|---|
| 2011/0189214 A1 | 8/2011 | Tsunoda et al. |
| 2011/0263012 A1 | 10/2011 | Nakamura et al. |
| 2012/0010090 A1 | 1/2012 | Nakamura et al. |
| 2012/0014996 A1 | 1/2012 | Nakamura et al. |
| 2012/0021946 A1 | 1/2012 | Nakamura et al. |

FOREIGN PATENT DOCUMENTS

| | | |
|---|---|---|
| EA | 008026 B1 | 2/2007 |
| EP | 2186889 A1 | 5/2010 |
| JP | 2004/500029 A | 1/2004 |
| JP | 2004/512824 A | 4/2004 |
| JP | 2006/500949 A | 1/2006 |
| WO | 98/53071 A1 | 11/1998 |
| WO | 00/78806 A1 | 12/2000 |
| WO | 01/00828 A2 | 1/2001 |
| WO | 01/22920 A2 | 4/2001 |
| WO | 02/04514 A2 | 1/2002 |
| WO | 02/094981 A2 | 11/2002 |
| WO | 03/025010 A2 | 3/2003 |
| WO | 03/037267 A2 | 5/2003 |
| WO | 03/105891 A2 | 12/2003 |
| WO | 2004/024766 A1 | 3/2004 |
| WO | 2004/031410 A2 | 4/2004 |
| WO | 2004/031413 A2 | 4/2004 |
| WO | 2004/055050 A2 | 7/2004 |
| WO | 2004/067023 A2 | 8/2004 |
| WO | 2004/080148 A2 | 9/2004 |
| WO | 2005/028676 A2 | 3/2005 |
| WO | 2005/089735 A2 | 9/2005 |
| WO | 2006/085684 A2 | 8/2006 |
| WO | 2007/013480 A2 | 2/2007 |
| WO | 2007/013665 A2 | 2/2007 |
| WO | 2007/013671 A2 | 2/2007 |
| WO | 2009/025117 A1 | 2/2009 |
| WO | 2009/153992 A1 | 12/2009 |
| WO | 2001/030329 A1 | 3/2011 |

OTHER PUBLICATIONS

Bodey et al (Anticancer Research 20: 2665-2676, 2000) (Year: 2000).*
Gao et al (J. Immunother. 23: 643-653, 2000) (Year: 2000).*
Morel et al (Immunity 12: 107-117, 2000) (Year: 2000).*
Celis (J. Clin. Invest. 2002, 110(12: 1765-1768) (Year: 2002).*
Boon et al (Ann. Rev. Innnnunol. 2006, 24: 175-208) (Year: 2006).*
U.S. Appl. No. 15/411,115, filed Jan. 20, 2017, 122 pages.
Adams, et al., "Prediction of binding to MHC class I molecules " *J Immunol Methods*, vol. 185(2), pp. 181-190 (Sep. 25, 1995).
Belli, et al., "Vaccination of Metastatic Melanoma Patients With Autologous Tumor-derived Heat Shock Protein gp96-Peptide Complexes: Clinical and Immunologic Findings," *J Clin Oncol.*, vol. 20(20), pp. 4169-4180 (Oct. 15, 2002).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Celts et al., "Identification of potential CTL epitopes of tumor-associated antigen MAGE-1 for five common HLA-A alleles," *Molecular Immunology*, vol. 31, Issue 18, Dec. 1994, pp. 1423-1430.
Coulie, et al., "Cytolytic T-cell responses of cancer patients vaccinated with a MAGE antigen," *Immunol Rev.*, vol. 188, pp. 33-42 (Oct. 2002).
Daigo, et al., "From cancer genomics to the cancer clinic: Novel biomarker discovery for lung cancer treatment " *INCA-NCRI 1st Joint Meeting on Cancer Genomics*, 44 pages (Jan. 4, 2007).
Daigo, et al., "From cancer genomics to the cancer clinic: New biomarker and therapeutic target discovery for lung cancer therapy," *The First JCA-AACR Special Joint Conference*, 49 pages (Mar. 2007).
Deluca, et al., "hNuf2 inhibition blocks stable kinetochore-microtubule attachment and induces mitotic cell death in HeLa cells," *J Cell Biol.*, vol. 159(4), pp. 549-555 (Epub Nov. 18, 2002, Nov. 25, 2002).
Deluca, et al., "Nuf2 and Heel Are Required for Retention of the Checkpoint Proteins Mad1 and Mad2 to Kinetochores," *Curr Biol.*, vol. 13(23), pp. 2103-2109 (Dec. 2, 2003).
Deluca, et al., "Hec1 and Nuf2 Are Core Components of the Kinetochore Outer Plate Essential for Organizing Microtubule Attachment Sites," *Mol Biol Cell*, vol. 16(2), pp. 519-531 (Feb. 2005).
Dermer, "Another Anniversary for the War on Cancer," *Bio/Technology*, vol. 12, p. 320 (Mar. 1994).
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Engelhard, "Structure of peptides associated with MHC class I molecules," *Curr Opin Immunol.*, vol. 6(1), pp. 13-23 (Feb. 1994).
Ezzell, "Cancer "Vaccines": An Idea Whose Time Has Come?," *J Nih Res.*, vol. 7, pp. 46-49 (1995).
Falk, et al., "Allele-specific motifs revealed by sequencing of self-peptides eluted from MHC molecules," *Nature*, vol. 351(6324), pp. 290-296 (May 23, 1991).
Fournier, et al., "Randomized clinical studies of anti-tumor vaccination: state of the art in 2008," Expert Review of Vaccines, vol. 8, Issue 1, 2009, pp. 51-56.
Freshney, et al., Culture of Animal Cells, A Manual of Basic Technique, Alan R. Liss, Inc., New York, pp. 3-4 (1983).
Fujie, et al., "A Mage-1 -Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).
Guo, et al., "Different length peptides bind to HLA-Aw68 similarly at their ends but bulge out in the middle," *Nature*, vol. 360(6402), pp. 364-366 (Nov. 26, 1992).
Gura, et al. "Systems for Identifying New Drugs are Often Faulty," *Science*, vol. 278(5340), pp. 1041-1042 (Nov. 7, 1997).
Harao, "Cell division cycle associated 1, an ideal lung cancer antigen for immunotherapy, identified using cDNA microarray analysis " *Doctor's Thesis, Graduate School of Medical Sciences*, 49 pages, Kumamoto University, Kumamoto, Japan, Retrieved from www.medic-kumamoto-u.ac.jp/dept/immunoge/frame/Thesis%20harao.pdf and www.medic.kumamoto-u.ac.jp/dept/immunoge/frame/top.html (Apr. 21, 2008, Retrieved Aug. 24, 2009).
Harao, et al., "CDCA1, a novel cancer-testis antigen useful for immunotherapy of lung cancer " *Abstract of the 66th Annual Meeting of the Japanese Cancer Association*, #P-294, pp. 163-164 (2007).
Harao, et al., "Identification of a novel cancer-testis antigen, CDCA1, that is useful for immunotherapy for lung cancer," *Journal of Japan Surgical Society*, vol. 109(Suppl 2), p. 282 (#SF-077-1) (Apr. 25, 2008).
Harao, et al., "Development of cancer immunotherapy targeting a novel cancer-testis antigen, CDCA1, that highly expresses in lung cancer," *Abstract of the 12th Annual Meeting of the Society for Fundamental Cancer Immunology*, p. 34 (Jun. 13, 2008).
Harao, et al., "HLA-A2-restricted CTL epitopes of a novel lung cancer-associated cancer testis antigen, cell division cycle associated 1, can induce tumor-reactive CTL," *Int J Cancer*, vol. 123(11), pp. 2616-2625 (Dec. 1, 2008).
Harris, Structure and Function of the p53 Tumor Suppressor Gene: Clues for Rational Cancer Therapeutic Strategies, *J Natl Cancer Inst.*, vol. 88(20), pp. 1442-1455 (Oct. 16, 1996).
Hayama, et al., "Isolation and characterization of a novel cancer-testis antigen IMS-CL54 that is frequently up-regulated in non-

(56) References Cited

OTHER PUBLICATIONS small cell lung cancer" *Proceedings of the 63rd Annual Meeting of the Japanese Cancer Association*, W-072, p. 54 (Aug. 2004).
Hayama, et al., "Isolation and characterization of novel cancer-testis antigens IMS-CL54 and IMS-CL81 that is frequently up-regulated in non-small cell lung cancer," *Proceedings of the 64th Annual Meeting of the Japanese Cancer Association*, W-344, p. 240 (Aug. 2005).
Hayama, et al., "Characterization of cancer-testis antigens IMS-CL54 and IMS-CL81 that play a role in lung cancer growth and their therapeutic application," *Proceedings of the 65th Annual Meeting of the Japanese Cancer Association*, P-237, p. 157 (2006).
Hayama, et al., "Activation IMS-CL54 and IMS-CL81 complex as promising therapeutic targets for lung cancer," *Proceedings of the American Association for Cancer Research (AACR)*, vol. 47, #2587, p. 610 (2006).
Hayama, et al., "Activation of CDCA1-KNTC2, Members of Centromere Protein Complex, Involved in Pulmonary Carcinogenesis," *Cancer Res.*, vol. 66(21), pp. 10339-10348 (Nov. 1, 2006).
Henderson, Sequence search result, ADJ21370, 2 pages (2010).
Hoffman, et al., "The Ability of Variant Peptides to Reverse the Nonresponsiveness of T Lymphocytes to the Wild-Type Sequence p53$_{264-272}$ Epitope," *J Immunol.*, vol. 168(3), pp. 1338-1347 (Feb. 1, 2002).
Hori, et al., "Dynamic behavior of Nuf2-Hec1 complex that localizes to the centrosome and centromere and is essential for mitotic progression in vertebrate cells," *J Cell Sci.*, vol. 116(Pt 16), pp. 3347-3362 (Epub Jun. 26, 2003, Aug. 15, 2003).
Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).
Jain, "Barriers to Drug Delivery in Solid Tumors," *Sci Am.*, vol. 271(1), pp. 58-65.
Johnson, et al., "The clinical impact of screening and other experimental tumor studies," *Cancer Treat Rev.*, vol. 2(1), pp. 1-31 (Mar. 1975).
Kakiuchi, et al., "Genome-Wide Analysis of Organ-Preferential Metastasis of Human Small Cell Lung Cancer in Mice," *Mol Cancer Res.*, vol. 1(7), pp. 485-499 (May 2003).
Kast et al., "Role of HLA-A Motifs in Identification of Potential CTL Epitopes in Human Papillomavirus Type 16 E6 and E7 Proteins", *J Immunol.*, vol. 152, No. 8, pp. 3904-3912 (1994).
Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Kikuchi, et al., "Expression profiles of non-small cell lung cancers on cDNA microarrays: Identification of genes for prediction of lymph-node metastasis and sensitivity to anti-cancer drugs," *Oncogene*, vol. 22(14), pp. 2192-2205 (Apr. 10, 2003).
Klebanoff, et al., "Therapeutic cancer vaccines: are we there yet?," Immunological Reviews, Special Issue: Vaccines, vol. 239, Issue 1, pp. 27-44, Jan. 2011.
Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).
Kubo, et al., "Definition of Specific Peptide Motifs for Four Major HLA-A Alleles," *J Immunol.*, vol. 152(8), pp. 3913-3924 (Apr. 15, 1994).
Liu, et al., "Mapping the assembly pathways that specify formation of the trilaminar kinetochore plates in human cells," *J Cell Biol.*, vol. 175(1), pp. 41-53 (Oct. 9, 2006).
Liu, et al., "Human NUF2 Interacts with Centromere-associated Protein E and Is Essential for a Stable Spindle Microtubule-Kinetochore Attachment," *J Biol Chem.*, vol. 282(29), pp. 21415-21424 (Jul. 20, 2007).
Ochoa-Garay, et al., "The ability of peptides to induce cytotoxic T cells in vitro does not strongly correlate with their affinity for the H-2Ld molecule: Implications for vaccine design and immunotherapy," *Molecular Immunology*, vol. 34, Issue 3, Feb. 1997, pp. 273-281.

Oiso, et al., "A Newly Identified Mage-3-Derived Epitope Recognized by HLA-A24-Restricted Cytotoxic T Lymphocytes," *Int J Cancer*, vol. 81(3), pp. 387-394 (May 5, 1999).
Rammensee, et al., "MHC ligands and peptide motifs: first listing," *Immunogenetics*, vol. 41(4), pp. 178-228 (1995).
Parker, et al., "Scheme for Ranking Potential HLA-A2 Binding Peptides Based on Independent Binding of Individual Peptides Side-Chains," *J Immunol.*, vol. 152(1), pp. 163-175 (Jan. 1, 1994).
Roitt, et al., Immunology, translation from English, M: Mir, pp. 10-13 (2000).
Roitt, et al., Immunology, translation from English, M: Mir, pp. 194, 159-162 (2000).
Roitt, et al., Immunology, translation from English, M: Mir, pp. 196-199 (2000).
Rosenberg, et al., "Cancer Immunotherapy: moving beyond current vaccines," *Nat Med.*, vol. 10(9), pp. 909-915 (Sep. 2004).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Schreiber, et al, "Tumor immunogenicity and responsiveness to cancer vaccine therapy: The state of the art," *Seminars in Immunology*, vol. 22, Issue 3, Jun. 2010, pp. 105-112.
Shastri, et al., "Presentation of Endogenous Peptide/MHC Class I Complexes is Profoundly Influenced by Specific C-Terminal Flanking Residues," *J Immunol.*, vol. 155(9), pp. 4339-4346 (Nov. 1, 1995).
Spitler, "Cancer Vaccines: The Interferon Analogy," *Cancer Biother.*, vol. 10(1), pp. 1-3 (Spring 1995).
Suzuki, et al., "Identification of COX17 as a Therapeutic Target for Non-Small Cell Lung Cancer," *Cancer Res.*, vol. 63(21), pp. 7038-7041 (Nov. 1, 2003).
Tanaka, et al., "Induction of Antitumor Cytotoxic T Lymphocytes with a MAGE-3-encoded Synthetic Peptide Presented by Human Leukocytes Antigen-A24 " *Cancer Res.*, vol. 57 (20), pp. 4465-4468 (Oct. 15, 1997).
Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).
Walker, "Drug Target Discovery by Gene Expression Analysis: Cell Cycle Genes," *Curr Cancer Drug Targets*, vol. 1(1), pp. 73-83 (May 2001).
Wigge, et al., "The Ndc80p Complex from *Saccharomyces cerevisiae* Contains Conserved Centromere Components and Has a Function in Chromosome Segregation," *J Cell Biol.*, vol. 152(2), pp. 349-360 (Jan. 22, 2001).
Zaremba, et al., "Identification of an Enhancer Agonist Cytotoxic T Lymphocytes Peptide from Human Carcinoembryonic Antigen," *Cancer Res.*, vol. 57(20), pp. 4570-4577 (Oct. 15, 1997).
Zips, et al., "New Anticancer Agents: In Vitro and In Vivo Evaluation " *In Vivo* Jan.-Feb. 2005 vol. 19 No. 1, 1-7.
Database printout: GSP: AAG74867, 2 pages, http://ibis/IBIS/exam/hitDetails.jsp?id=11808362 (downloaded Sep. 28, 2010).
U.S. Appl. No. 13/536,327, 204 pages, filed Jun. 28, 2012.
U.S. Appl. No. 14/413,413, filed Jan. 7, 2015,187 pages.
International Search Report for PCT/JP2009/002771, 7 pages (dated Jan. 9, 2009).
Genbank: AAY06266.1, downloaded from http://ncbi.nlm.nih.gov/protein/AAY06266, 1 page, downloaded on Sep. 30, 2013.
Score Search Results Details for Application 11913142 and Search Result Jun. 3, 2010, 6 pages, downloaded on Jul. 5, 2010.
U.S. Appl. No. 15/500,906, filed Jan. 31, 2017, 109 pages.
Geneseq Acc. No. ADS11001 (2007)/Genbank gill 7968353 (Accession No. NP_113611.2) Mar. 17, 2013.
Obara, et al; Phase I clin. trial of cell division assoc. 1 (CDCA1) peptide vaccination for castration resistant prostate cancer; Cancer Sci; Jul. 2017; vol. 108:7; 1452-1457.

\* cited by examiner

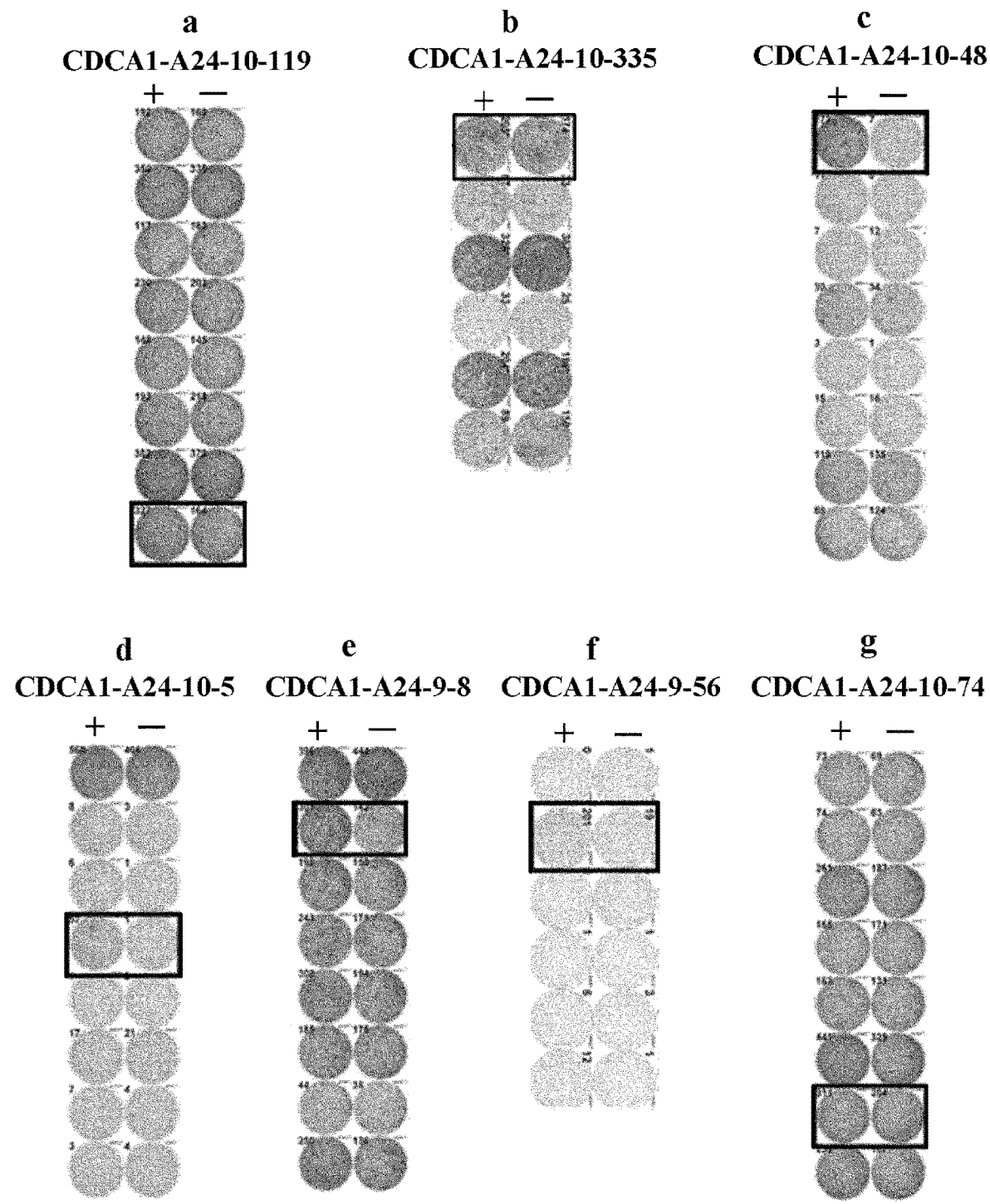

[Fig. 2]
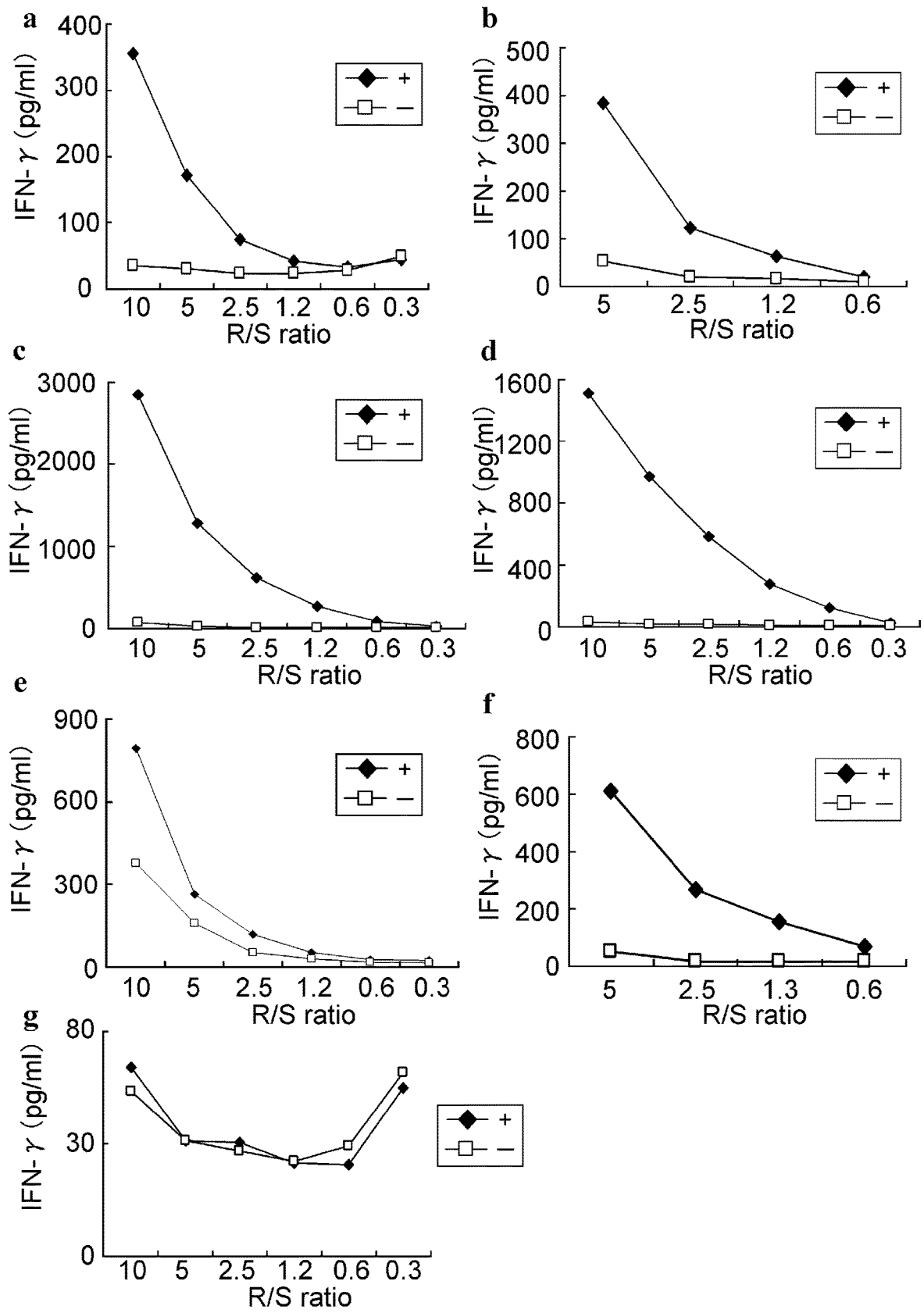

[Fig. 3]
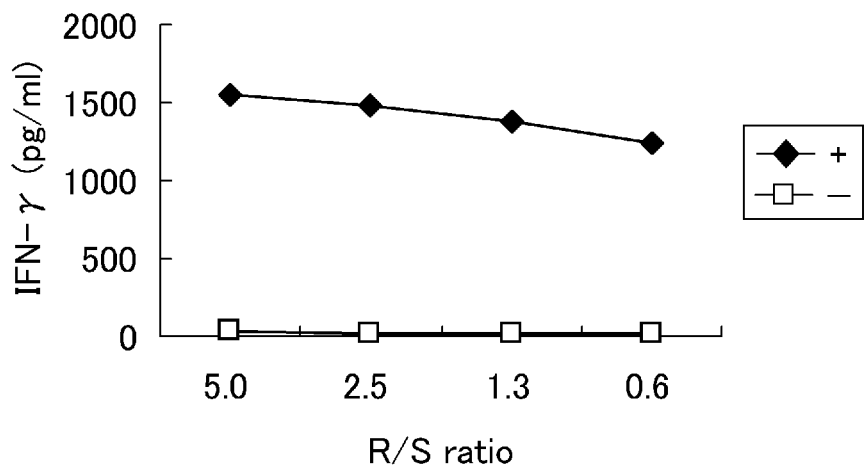
[Fig. 4]
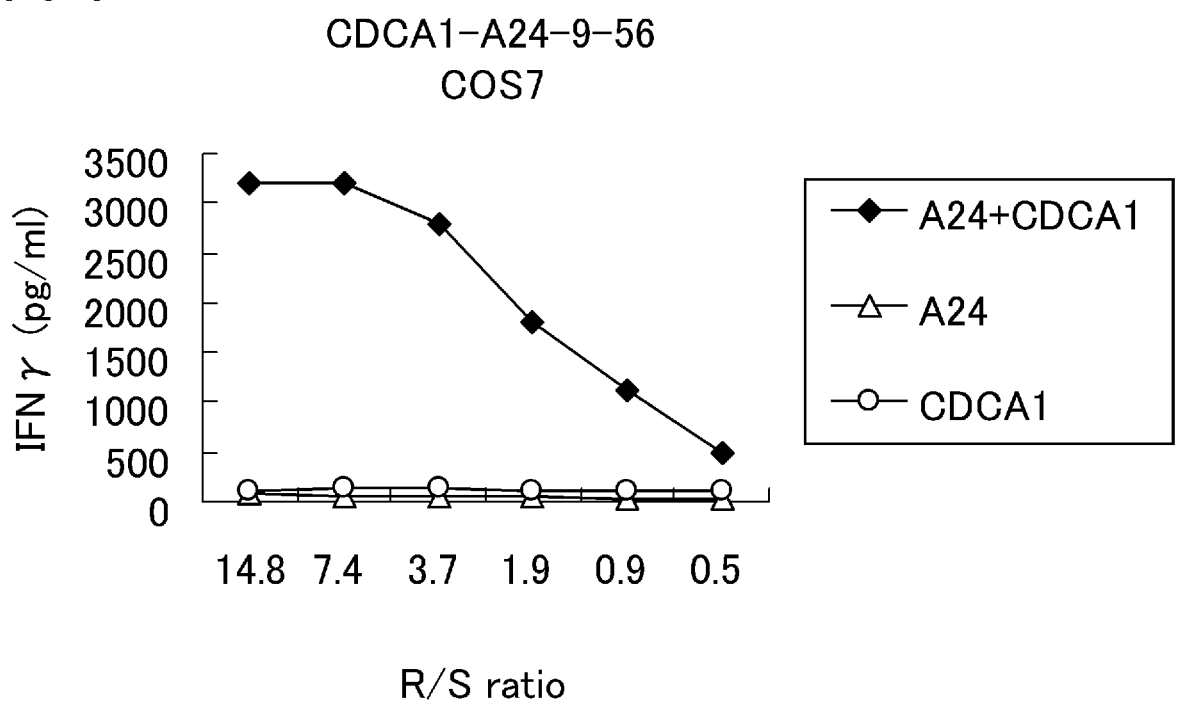

SEQUENCE LISTING

<160> NUMBER OF SEQ ID NOS: 35

<210> SEQ ID NO 1
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 1

Leu Tyr Pro Asn Pro Lys Pro Glu Val Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 2

Met Tyr Pro His Leu Met Glu Gly Phe Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 3

Arg Phe Leu Ser Gly Ile Ile Asn Phe Ile
1               5                   10

<210> SEQ ID NO 4
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 4

Lys Thr Glu Glu Asn Ser Phe Lys Arg Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 5

Lys Tyr His Asp Gly Ile Glu Lys Ala Ala
1               5                   10

<210> SEQ ID NO 6
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 6

Lys Gln Leu Ser Asp Gly Ile Gln Glu Leu
1               5                   10

```
<210> SEQ ID NO 7
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 7

Phe Tyr Met Met Pro Val Asn Ser Glu Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 8

Leu Tyr Gln Lys Lys Ile Gln Asp Leu Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 9

Lys Leu Ala Ser Ile Leu Lys Glu Ser Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 10

Lys Ser Ser Ala Asp Lys Met Gln Gln Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 11

Ile Tyr Met Arg Ala Leu Gln Ile Val Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 12

Asp Gly Ile Gln Glu Leu Gln Gln Ser Leu
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 13

Val Ser Leu Lys Glu Ile Gln Glu Ser Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 14

Ser Phe Pro Arg Tyr Asn Val Ala Glu Ile
1               5                   10

<210> SEQ ID NO 15
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 15

Ile Asn Gln Glu Ile Gln Lys Ile Lys Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 16

Asp Gln Ile Glu Ser Asp Glu Ser Glu Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 17

Asn Leu Val Thr His Leu Asp Ser Phe Leu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 18

Gln Tyr Lys Arg Thr Val Ile Glu Asp Cys
1               5                   10
```

```
<210> SEQ ID NO 19
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 19

Leu Tyr Gln Lys Lys Ile Gln Asp Leu
1               5

<210> SEQ ID NO 20
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 20

Ile Tyr Gly Asp Ser Val Asp Cys Leu
1               5

<210> SEQ ID NO 21
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 21

Met Tyr Pro His Leu Met Glu Gly Phe
1               5

<210> SEQ ID NO 22
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 22

Arg Tyr Asn Val Ala Glu Ile Val Ile
1               5

<210> SEQ ID NO 23
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 23

Val Tyr Gly Ile Arg Leu Glu His Phe
1               5

<210> SEQ ID NO 24
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 24

Ile Phe Leu Asn Leu Lys Thr Ala Leu
1               5

<210> SEQ ID NO 25
```

```
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 25

Arg Phe Leu Ser Gly Ile Ile Asn Phe
1               5

<210> SEQ ID NO 26
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 26

Gln Tyr Lys Ser Ser Ala Asp Lys Met
1               5

<210> SEQ ID NO 27
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 27

Lys Ser Gln Glu Ile Phe Leu Asn Leu
1               5

<210> SEQ ID NO 28
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 28

Asp Phe His Gln Lys Thr Ile Val Leu
1               5

<210> SEQ ID NO 29
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 29

Lys Tyr Glu Ile Tyr Gly Asp Ser Val
1               5

<210> SEQ ID NO 30
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 30

Lys Tyr His Asp Gly Ile Glu Lys Ala
1               5

<210> SEQ ID NO 31
<211> LENGTH: 9
```

```
<212> TYPE: PRT
<213> ORGANISM: Artificial Sequence
<220> FEATURE:
<223> OTHER INFORMATION: An artificially synthesized peptide sequence

<400> SEQUENCE: 31

Val Tyr Glu Arg Val Thr Thr Ile Asn
1               5

<210> SEQ ID NO 32
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 32

Gly Ile Gln Glu Leu Gln Gln Ser Leu
1               5

<210> SEQ ID NO 33
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 33

Ile Tyr Met Arg Ala Leu Gln Ile Val
1               5

<210> SEQ ID NO 34
<211> LENGTH: 1980
<212> TYPE: DNA
<213> ORGANISM: Homo sapiens
<220> FEATURE:
<221> NAME/KEY: CDS
<222> LOCATION: (301)..(1695)

<400> SEQUENCE: 34
gcggaatggg gcgggacttc cagtaggagg cggcaagttt gaaaagtgat gacggttgac      60
gtttgctgat ttttgacttt gcttgtagct gctccccgaa ctcgccgtct tcctgtcggc     120
ggccggcact gtaggtgagc gcgagaggac ggaggaagga agcctgcaga cagacgcctt     180
ctccatccca aggcgcgggc aggtgccggg acgctgggcc tggcggtgtt ttcgtcgtgc     240
tcagcggtgg gaggaggcgg aagaaaccag agcctgggag attaacagga aacttccaag     300 atg gaa act ttg tct ttc ccc aga tat aat gta gct gag att gtg att      348
Met Glu Thr Leu Ser Phe Pro Arg Tyr Asn Val Ala Glu Ile Val Ile
1               5                   10                  15 cat att cgc aat aag atc tta aca gga gct gat ggt aaa aac ctc acc      396
His Ile Arg Asn Lys Ile Leu Thr Gly Ala Asp Gly Lys Asn Leu Thr
                20                  25                  30 aag aat gat ctt tat cca aat cca aag cct gaa gtc ttg cac atg atc      444
Lys Asn Asp Leu Tyr Pro Asn Pro Lys Pro Glu Val Leu His Met Ile
            35                  40                  45 tac atg aga gcc tta caa ata gta tat gga att cga ctg gaa cat ttt      492
Tyr Met Arg Ala Leu Gln Ile Val Tyr Gly Ile Arg Leu Glu His Phe
        50                  55                  60 tac atg atg cca gtg aac tct gaa gtc atg tat cca cat tta atg gaa      540
Tyr Met Met Pro Val Asn Ser Glu Val Met Tyr Pro His Leu Met Glu
65                  70                  75                  80 ggc ttc tta cca ttc agc aat tta gtt act cat ctg gac tca ttt ttg      588
Gly Phe Leu Pro Phe Ser Asn Leu Val Thr His Leu Asp Ser Phe Leu
```

-continued

```
                     85                  90                  95
cct atc tgc cgg gtg aat gac ttt gag act gct gat att cta tgt cca     636
Pro Ile Cys Arg Val Asn Asp Phe Glu Thr Ala Asp Ile Leu Cys Pro
            100                 105                 110 aaa gca aaa cgg aca agt cgg ttt tta agt ggc atc atc aac ttt att     684
Lys Ala Lys Arg Thr Ser Arg Phe Leu Ser Gly Ile Ile Asn Phe Ile
        115                 120                 125 cac ttc aga gaa gca tgc cgt gaa acg tat atg gaa ttt ctt tgg caa     732
His Phe Arg Glu Ala Cys Arg Glu Thr Tyr Met Glu Phe Leu Trp Gln
    130                 135                 140 tat aaa tcc tct gcg gac aaa atg caa cag tta aac gcc gca cac cag     780
Tyr Lys Ser Ser Ala Asp Lys Met Gln Gln Leu Asn Ala Ala His Gln
145                 150                 155                 160 gag gca tta atg aaa ctg gag aga ctt gat tct gtt cca gtt gaa gag     828
Glu Ala Leu Met Lys Leu Glu Arg Leu Asp Ser Val Pro Val Glu Glu
                165                 170                 175 caa gaa gag ttc aag cag ctt tca gat gga att cag gag cta caa caa     876
Gln Glu Glu Phe Lys Gln Leu Ser Asp Gly Ile Gln Glu Leu Gln Gln
            180                 185                 190 tca cta aat cag gat ttt cat caa aaa acg ata gtg ctg caa gag gga     924
Ser Leu Asn Gln Asp Phe His Gln Lys Thr Ile Val Leu Gln Glu Gly
        195                 200                 205 aat tcc caa aag aag tca aat att tca gag aaa acc aag cgt ttg aat     972
Asn Ser Gln Lys Lys Ser Asn Ile Ser Glu Lys Thr Lys Arg Leu Asn
    210                 215                 220 gaa cta aaa ttg tcg gtg gtt tct ttg aaa gaa ata caa gag agt ttg    1020
Glu Leu Lys Leu Ser Val Val Ser Leu Lys Glu Ile Gln Glu Ser Leu
225                 230                 235                 240 aaa aca aaa att gtg gat tct cca gag aag tta aag aat tat aaa gaa    1068
Lys Thr Lys Ile Val Asp Ser Pro Glu Lys Leu Lys Asn Tyr Lys Glu
                245                 250                 255 aaa atg aaa gat acg gtc cag aag ctt aaa aat gcc aga caa gaa gtg    1116
Lys Met Lys Asp Thr Val Gln Lys Leu Lys Asn Ala Arg Gln Glu Val
            260                 265                 270 gtg gag aaa tat gaa atc tat gga gac tca gtt gac tgc ctg cct tca    1164
Val Glu Lys Tyr Glu Ile Tyr Gly Asp Ser Val Asp Cys Leu Pro Ser
        275                 280                 285 tgt cag ttg gaa gtg cag tta tat caa aag aaa ata cag gac ctt tca    1212
Cys Gln Leu Glu Val Gln Leu Tyr Gln Lys Lys Ile Gln Asp Leu Ser
    290                 295                 300 gat aat agg gaa aaa tta gcc agt atc tta aag gag agc ctg aac ttg    1260
Asp Asn Arg Glu Lys Leu Ala Ser Ile Leu Lys Glu Ser Leu Asn Leu
305                 310                 315                 320 gag gac caa att gag agt gat gag tca gaa ctg aag aaa ttg aag act    1308
Glu Asp Gln Ile Glu Ser Asp Glu Ser Glu Leu Lys Lys Leu Lys Thr
                325                 330                 335 gaa gaa aat tcg ttc aaa aga ctg atg att gtg aag aag gaa aaa ctt    1356
Glu Glu Asn Ser Phe Lys Arg Leu Met Ile Val Lys Lys Glu Lys Leu
            340                 345                 350 gcc aca gca caa ttc aaa ata aat aag aag cat gaa gat gtt aag caa    1404
Ala Thr Ala Gln Phe Lys Ile Asn Lys Lys His Glu Asp Val Lys Gln
        355                 360                 365 tac aaa cgc aca gta att gag gat tgc aat aaa gtt caa gaa aaa aga    1452
Tyr Lys Arg Thr Val Ile Glu Asp Cys Asn Lys Val Gln Glu Lys Arg
    370                 375                 380 ggt gct gtc tat gaa cga gta acc aca att aat caa gaa atc caa aaa    1500
Gly Ala Val Tyr Glu Arg Val Thr Thr Ile Asn Gln Glu Ile Gln Lys
385                 390                 395                 400 att aaa ctt gga att caa caa cta aaa gat gct gct gaa agg gag aaa    1548
```

-continued

```
Ile Lys Leu Gly Ile Gln Gln Leu Lys Asp Ala Ala Glu Arg Glu Lys
                405                 410                 415 ctg aag tcc cag gaa ata ttt cta aac ttg aaa act gct ttg gag aaa      1596
Leu Lys Ser Gln Glu Ile Phe Leu Asn Leu Lys Thr Ala Leu Glu Lys
        420                 425                 430 tac cac gac ggt att gaa aag gca gca gag gac tcc tat gct aag ata      1644
Tyr His Asp Gly Ile Glu Lys Ala Ala Glu Asp Ser Tyr Ala Lys Ile
            435                 440                 445 gat gag aag aca gct gaa ctg aag agg aag atg ttc aaa atg tca acc      1692
Asp Glu Lys Thr Ala Glu Leu Lys Arg Lys Met Phe Lys Met Ser Thr
        450                 455                 460 tga ttaacaaaat tacatgtctt tttgtaaatg gcttgccatc ttttaatttt           1745
ctatttagaa agaaaagttg aagcgaatgg aagtatcaga agtaccaaat aatgttggct    1805
tcatcagttt ttatacactc tcataagtag ttaataagat gaattaatg taggctttta     1865 ttaatttata attaaaataa cttgtgcagc tattcatgtc tctactctgc cccttgttgt    1925
aaatagtttg agtaaaacaa aactagttac ctttgaaata tatatatttt tttct         1980
```

<210> SEQ ID NO 35
<211> LENGTH: 464
<212> TYPE: PRT
<213> ORGANISM: Homo sapiens

<400> SEQUENCE: 35

```
Met Glu Thr Leu Ser Phe Pro Arg Tyr Asn Val Ala Glu Ile Val Ile
1               5                   10                  15

His Ile Arg Asn Lys Ile Leu Thr Gly Ala Asp Gly Lys Asn Leu Thr
            20                  25                  30

Lys Asn Asp Leu Tyr Pro Asn Pro Lys Pro Glu Val Leu His Met Ile
        35                  40                  45

Tyr Met Arg Ala Leu Gln Ile Val Tyr Gly Ile Arg Leu Glu His Phe
    50                  55                  60

Tyr Met Met Pro Val Asn Ser Glu Val Met Tyr Pro His Leu Met Glu
65                  70                  75                  80

Gly Phe Leu Pro Phe Ser Asn Leu Val Thr His Leu Asp Ser Phe Leu
                85                  90                  95

Pro Ile Cys Arg Val Asn Asp Phe Glu Thr Ala Asp Ile Leu Cys Pro
            100                 105                 110

Lys Ala Lys Arg Thr Ser Arg Phe Leu Ser Gly Ile Ile Asn Phe Ile
        115                 120                 125

His Phe Arg Glu Ala Cys Arg Glu Thr Tyr Met Glu Phe Leu Trp Gln
    130                 135                 140

Tyr Lys Ser Ser Ala Asp Lys Met Gln Gln Leu Asn Ala Ala His Gln
145                 150                 155                 160

Glu Ala Leu Met Lys Leu Glu Arg Leu Asp Ser Val Pro Val Glu Glu
                165                 170                 175

Gln Glu Glu Phe Lys Gln Leu Ser Asp Gly Ile Gln Glu Leu Gln Gln
            180                 185                 190

Ser Leu Asn Gln Asp Phe His Gln Lys Thr Ile Val Leu Gln Glu Gly
        195                 200                 205

Asn Ser Gln Lys Lys Ser Asn Ile Ser Glu Lys Thr Lys Arg Leu Asn
    210                 215                 220

Glu Leu Lys Leu Ser Val Val Ser Leu Lys Glu Ile Gln Glu Ser Leu
225                 230                 235                 240

Lys Thr Lys Ile Val Asp Ser Pro Glu Lys Leu Lys Asn Tyr Lys Glu
```

```
                    245                 250                 255
Lys Met Lys Asp Thr Val Gln Lys Leu Lys Asn Ala Arg Gln Glu Val
            260                 265                 270

Val Glu Lys Tyr Glu Ile Tyr Gly Asp Ser Val Asp Cys Leu Pro Ser
            275                 280                 285

Cys Gln Leu Glu Val Gln Leu Tyr Gln Lys Lys Ile Gln Asp Leu Ser
            290                 295                 300

Asp Asn Arg Glu Lys Leu Ala Ser Ile Leu Lys Glu Ser Leu Asn Leu
305                 310                 315                 320

Glu Asp Gln Ile Glu Ser Asp Glu Ser Glu Leu Lys Lys Leu Lys Thr
                325                 330                 335

Glu Glu Asn Ser Phe Lys Arg Leu Met Ile Val Lys Lys Glu Lys Leu
            340                 345                 350

Ala Thr Ala Gln Phe Lys Ile Asn Lys Lys His Glu Asp Val Lys Gln
            355                 360                 365

Tyr Lys Arg Thr Val Ile Glu Asp Cys Asn Lys Val Gln Glu Lys Arg
            370                 375                 380

Gly Ala Val Tyr Glu Arg Val Thr Thr Ile Asn Gln Glu Ile Gln Lys
385                 390                 395                 400

Ile Lys Leu Gly Ile Gln Gln Leu Lys Asp Ala Ala Glu Arg Glu Lys
                405                 410                 415

Leu Lys Ser Gln Glu Ile Phe Leu Asn Leu Lys Thr Ala Leu Glu Lys
            420                 425                 430

Tyr His Asp Gly Ile Glu Lys Ala Ala Glu Asp Ser Tyr Ala Lys Ile
            435                 440                 445

Asp Glu Lys Thr Ala Glu Leu Lys Arg Lys Met Phe Lys Met Ser Thr
450                 455                 460
```

CDCA1 EPITOPE PEPTIDES AND VACCINES CONTAINING THE SAME

The present application is a Divisional of U.S. application Ser. No. 12/999,051, filed Apr. 22, 2011, which is a U.S. National Stage Application of PCT/JP2009/002771, filed Jun. 18, 2009, which claims the benefit of U.S. Provisional Application No. 61/074,062, filed Jun. 19, 2008, and 61/197,599, filed Oct. 28, 2008, the entire contents of which are incorporated by reference herein.

TECHNICAL FIELD

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8 positive cytotoxic T lymphocytes (CTLs) recognize epitope peptides derived from the tumor-associated antigens (TAAs) found on major histocompatibility complex (MHC) class I molecule, and then kill the tumor cells. Since the discovery of the melanoma antigen (MAGE) family as the first example of TAAs, many other TAAs have been discovered, primarily through immunological approaches (Boon T, Int J Cancer 1993 May 8, 54(2): 177-80; Boon T & van der Bruggen P, J Exp Med 1996 Mar. 1, 183(3): 725-9). Some of these TAAs are currently undergoing clinical development as immunotherapeutic targets.

Identification of new TAAs capable of inducing potent and specific anti-tumor immune responses, warrants further development and clinical application of peptide vaccination strategies for various types of cancer (Harris C C, J Natl Cancer Inst 1996 Oct. 16, 88(20): 1442-55; Butterfield L H et al., Cancer Res 1999 Jul. 1, 59(13): 3134-42; Vissers J L et al., Cancer Res 1999 Nov. 1, 59(21): 5554-9; van der Burg S H et al., J Immunol 1996 May 1, 156(9): 3308-14; Tanaka F et al., Cancer Res 1997 Oct. 15, 57(20): 4465-8; Fujie T et al., Int J Cancer 1999 Jan. 18, 80(2): 169-72; Kikuchi M et al., Int J Cancer 1999 May 5, 81(3): 459-66; Oiso M et al., Int J Cancer 1999 May 5, 81(3): 387-94). To date, there have been several reports of clinical trials using these tumor-associated antigen derived peptides. Unfortunately, only a low objective response rate has been observed in these cancer vaccine trials so far (Belli F et al., J Clin Oncol 2002 Oct. 15, 20(20): 4169-80; Coulie P G et al., Immunol Rev 2002 October, 188: 33-42; Rosenberg S A et al., Nat Med 2004 September, 10(9): 909-15).

TAAs which are indispensable for proliferation and survival of cancer cells are valiant as targets for immunotherapy, because the use of such TAAs may minimize the well-described risk of immune escape of cancer cells attributable to deletion, mutation, or down-regulation of TAAs as a consequence of therapeutically driven immune selection.

CDCA1, cell division cycle associated 1, was identified as a member of a class of genes that are coexpressed with cell cycle genes, such as CDC2, cyclin, topoisomerase II and the others (Walker et al., Curr Cancer Drug Targets 2001 May; 1(1):73-83). CDCA1 in particular was found to be associated with centromeres of mitotic HeLa cells and was therefore considered a functional homologue of yeast Nuf2 (J Cell Biol 2001 Jan. 22; 152(2):349-60).

In addition, through gene expression profile analysis using a genome-wide cDNA microarray containing 23,040 genes (Cancer Res 2006 Nov. 1; 66(21):10339-48), CDCA1 has also been identified as a novel molecule up-regulated in breast cancer (WO2005/028676), bladder cancer (WO2006/085684), esophageal cancer (WO2007/013671), small cell lung cancer (SCLC) (WO2007/013665) and non-small cell lung cancer (NSCLC) (WO2005/089735), the contents of such disclosure being incorporated by reference herein. Expression of CDCA1 was particularly up-regulated in SCLC, NSCLC and tumor cell lines, though no expression was detected except testis among 23 normal tissues. Furthermore, down-regulation of CDCA1 expression by siRNA caused cell growth suppression in CDCA1 expressing lung cancer cell lines (WO2005/089735).

Taken together, this data suggests that CDCA1 is a novel, potentially universal oncoantigen. Accordingly, epitope peptides derived from CDCA1 may be applicable as cancer immunotherapeutics for the treatment of a wide array of cancers.

SUMMARY OF INVENTION

The present invention is based in part on the discovery of the suitable epitope peptides that may serve as targets of immunotherapy. Recognizing that CDCA1 are up-regulated in a number of cancer types, including breast cancer, bladder cancer, non-small cell lung cancer, small cell lung cancer and esophageal cancer, the present invention targets this cell division cycle associated 1 (CDCA1) (SEQ ID NO: 35 encoded by the gene of GenBank Accession No. NM_145697 (SEQ ID NO: 34)) for further analysis. In particular, CDCA1 gene products containing epitope peptides that elicit CTLs specific to the corresponding molecules were selected. Peripheral blood mononuclear cells (PBMCs) obtained from a healthy donor were stimulated using HLA-A*2402 binding candidate peptides derived from CDCA1. CTLs that specifically recognize HLA-A24 positive target cells pulsed with the respective candidate peptides were established, and HLA-A24 restricted epitope peptides that can induce potent and specific immune responses against CDCA1 were identified. These results demonstrate that CDCA1 is strongly immunogenic and the epitopes thereof are effective targets for tumor immunotherapy.

Accordingly, it is an object of the present invention to provide peptides having CTL inducibility as well as an amino acid sequence selected from among SEQ ID NOs: 3, 4, 11, 14, 22 and 23. The present invention contemplates modified peptides, having an amino acid sequence of SEQ ID NOs: 3, 4, 11, 14, 22 or 23, wherein one, two or more amino acids are substituted, incorporated, deleted or added, so long as the modified peptides retain the original CTL inducibility.

When administered to a subject, the present peptides are presented on the surface of antigen-presenting cells or exosomes and then induce CTLs targeting the respective peptides. Therefore, it is an object of the present invention to provide antigen-presenting cells and exosomes presenting any of the present peptides, as well as methods for inducing antigen-presenting cells.

An anti-tumor immune response is induced by the administration of the present CDCA1 polypeptides or polynucleotide encoding the polypeptides, as well as exosomes and antigen-presenting cells which present the CDCA1 polypeptides. Therefore, it is an object of the present invention to provide pharmaceutical agents containing the polypeptides of the present invention or polynucleotides encoding them, as well as the exosomes and antigen-presenting cells containing such as their active ingredients. The pharmaceutical agents of the present invention find particular utility as vaccines.

It is a further object of the present invention to provide methods for the treatment and/or prophylaxis of (i.e., preventing) cancers (tumors), and/or prevention of postoperative recurrence thereof, as well as methods for inducing CTLs, methods for inducing anti-tumor immunity, which methods include the step of administering the CDCA1 polypeptides, polynucleotides encoding CDCA1 polypeptides, exosomes or the antigen-presenting cells presenting CDCA1 polypeptides or the pharmaceutical agents of the invention. In addition, the CTLs of the invention also find use as vaccines against cancer. Examples of cancers contemplated by the present invention include, but are not limited to breast cancer, bladder cancer, esophageal cancer, small cell lung cancer (SCLC) and non-small cell lung cancer (NSCLC).

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIG. 1 is composed of a series of photographs, (a) to (g), depicting the results of an IFN-gamma ELISPOT assay on CTLs that were induced with peptides derived from CDCA1. The CTLs in well numbers #8 stimulated with CDCA1-A24-10-119 (SEQ ID NO: 3) (a), #1 with CDCA1-A24-10-335 (SEQ ID NO: 4) (b), #1 with CDCA1-A24-10-48 (SEQ ID NO: 11) (c), #4 with CDCA1-A24-10-5 (SEQ ID NO: 14) (d), #2 with CDCA1-A24-9-8 (SEQ ID NO: 22) (e) and #2 with CDCA1-A24-9-56 (SEQ ID NO: 23) (f) showed potent IFN-gamma production as compared with the control, respectively. In contrast, no specific IFN-gamma production against peptide-pulsed target cells was detected in the CTLs stimulated with CDCA1-A24-10-74 (SEQ ID NO: 2) (g). The cells in the wells denoted with a rectangular box were expanded to establish CTL lines. In the figures, "+" indicates the IFN-gamma production against target cells pulsed with the appropriate peptide, and "−" indicates the IFN-gamma production against target cells not pulsed with any peptides.

FIG. 2 is composed of a series of line graphs, (a) to (g), representing the results of an IFN-gamma ELISA assay on CTL lines established with CDCA1-A24-10-119 (SEQ ID NO: 3) (a), CDCA1-A24-10-335 (SEQ ID NO: 4) (b), CDCA1-A24-10-48 (SEQ ID NO: 11) (c), CDCA1-A24-10-5 (SEQ ID NO: 14) (d), CDCA1-A24-9-8 (SEQ ID NO: 22) (e) and CDCA1-A24-9-56 (SEQ ID NO: 23) (0 in the above IFN-gamma ELISA assay. The results demonstrate that CTL lines established by stimulation with each peptide showed potent IFN-gamma production as compared with the control. In contrast, no specific IFN-gamma production against peptide-pulsed target cells was observed in the CTL line established with CDCA1-A24-10-74 (SEQ ID NO: 2) (g). In the figures, "+" indicates the IFN-gamma production against target cells pulsed with the appropriate peptide, and "−" indicates the IFN-gamma production against target cells not pulsed with any peptides.

FIG. 3 is a line graph depicting the IFN-gamma production of the CTL clone established by limiting dilution from the CTL line stimulated with SEQ ID NO: 23. The results demonstrate that the CTL clone established by stimulation with SEQ ID NO: 23 showed potent IFN-gamma production as compared with the control. In the figure, "+" indicates the IFN-gamma production against target cells pulsed with SEQ ID NO: 23s and "−" indicates the IFN-gamma production against target cells not pulsed with any peptides.

FIG. 4 is a line graph depicting the specific CTL activity against the target cells that exogenously express CDCA1 and HLA-A*2402. The CTL clone established with CDCA1-A24-9-56 (SEQ ID NO: 23) showed high specific CTL activity against COS7 cells transfected with both CDCA1 and HLA-A*2402 (lozenge). In contrast, no significant specific CTL activity was detected against target cells expressing either HLA-A*2402 (triangle) or CDCA1 (circle).

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

I. Definitions

Unless otherwise defined, all technical and scientific terms used herein have the same meaning as commonly understood by one of ordinary skill in the art to which the present invention belongs. However, in case of conflict, the present specification, including definitions, will control.

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide", "nucleotide" and "nucleic acid" are used interchangeably herein and, unless otherwise specifically indicated, are referred to by their commonly accepted single-letter codes.

Unless otherwise defined, the term "cancer" refers to cancers overexpressing CDCA1 gene, including, for example, breast cancer, bladder cancer, esophageal cancer, small cell lung cancer (SCLC) and non-small cell lung cancer (NSCLC).

Unless otherwise defined, the term "cytotoxic T lymphocyte", "cytotoxic T cell" and "CTL" are used interchangeably herein and, otherwise specifically indicated, refer to a sub-group of T lymphocytes that are capable of recognizing non-self cells (e.g., tumor cells, virus-infected cells) and inducing the death of such cells.

II. Peptides

To demonstrate that peptides derived from CDCA1 function as an antigen recognized by cytotoxic T lymphocytes (CTLs), peptides derived from CDCA1 (SEQ ID NO: 35) were analyzed to determine whether they were antigen epitopes restricted by HLA-A24 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A24 binding peptides derived from CDCA1 were identified based on their binding affinities to HLA-A24. After in vitro stimulation of T-cells by dendritic cells (DCs) loaded with these peptides, CTLs were successfully established using each of the following peptides:
CDCA1-A24-10-119 (SEQ ID NO: 3),
CDCA1-A24-10-335 (SEQ ID NO: 4),
CDCA1-A24-10-48 (SEQ ID NO: 11),
CDCA1-A24-10-5 (SEQ ID NO: 14),
CDCA1-A24-9-8 (SEQ ID NO: 22),
and
CDCA1-A24-9-56 (SEQ ID NO: 23).

These established CTLs show potent specific CTL activity against target cells pulsed with respective peptides. These results herein demonstrate that CDCA1 is an antigen recognized by CTLs and that the peptides are epitope peptides of CDCA1 restricted by HLA-A24.

Since the CDCA1 gene is over-expressed in most cancer tissues, including, for example, breast cancer, bladder cancer, esophageal cancer, small cell lung cancer (SCLC) and non-small cell lung cancer (NSCLC), it represents a good target for immunotherapy. Thus, the present invention provides nonapeptides (peptides consisting of nine amino acid residues) and decapeptides (peptides consisting of ten amino acid residues) corresponding to CTL-recognized epitopes of CDCA1. Particularly preferred examples of nonapeptides and decapeptides of the present invention include those peptides consisting of the amino acid sequence selected from among SEQ ID NOs: 3, 4, 11, 14, 22 and 23.

Generally, software programs presently available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in Parker K C et al., J Immunol 1994 Jan. 1, 152(1): 163-75; and Kuzushima K et al., Blood 2001, 98(6): 1872-81. The methods for determining binding affinity is described, for example, in the Journal of Immunological Methods, 1995, 185: 181-190 and Protein Science, 2000, 9: 1838-1846. Thus, the present invention encompasses peptides of CDCA1 which are determined to bind with HLA antigens identified using such known programs.

The nonapeptides and decapeptides of the present invention can be optionally flanked with additional amino acid residues so long as the peptide retains its CTL inducibility. Such peptides having CTL inducibility are typically, less than about 40 amino acids, often less than about 20 amino acids, usually less than about 15 amino acids. The particular amino acid sequence(s) flanking the peptides consisting of the amino acid sequence selected from among SEQ ID NOs: 3, 4, 11, 14, 22 and 23 are not limited and can be composed of any kind of amino acids, so long as it does not impair the CTL inducibility of the original peptide. Thus, the present invention also provides peptides having CTL inducibility and an amino acid sequence selected from among SEQ ID NOs: 3, 4, 11, 14, 22 and 23.

In general, the modification of one, two, or more amino acids in a protein will not influence the function of the protein, and in some cases will even enhance the desired function of the original protein. In fact, modified peptides (i.e., peptides composed of an amino acid sequence in which one, two or several amino acid residues have been modified (i.e., substituted, added, deleted or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NO: 3, 4, 11, 14, 22 and 23, wherein one, two or even more amino acids are added, inserted, deleted and/or substituted.

Those of skilled in the art recognize that individual additions or substitutions to an amino acid sequence which alter a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the modified peptide retains the CTL inducibility of the original peptide. Furthermore, modified peptides should not exclude CTL inducible peptides of polymorphic variants, interspecies homologues, and alleles of CDCA1.

To retain the requisite CTL inducibility one can modify (insert, add, deletion and/or substitute) a small number (for example, 1, 2 or several) or a small percentage of amino acids. Herein, the term "several" means 5 or fewer amino acids, for example, 3 or fewer. The percentage of amino acids to be modified is preferably 20% or less, more preferably, 15% of less, even more preferably 10% or less or 1 to 5%.

Homology analysis of preferred peptides of the present invention, CDCA1-A24-10-119 (SEQ ID NO: 3), CDCA1-A24-10-335 (SEQ ID NO: 4), CDCA1-A24-10-48 (SEQ ID NO: 11), CDCA1-A24-10-5 (SEQ ID NO: 14), CDCA1-A24-9-8 (SEQ ID NO: 22) and CDCA1-A24-9-56 (SEQ ID NO: 23), confirmed that these peptides do not have significant homology with peptides derived from any other known human gene products. Thus, the possibility of these peptides generating unknown or undesired immune responses when used for immunotherapy is significantly lowered. Accordingly, these peptides are expected to be highly useful for eliciting immunity in cancer patients against CDCA1.

When used in the context of immunotherapy, the peptides of the present invention should be presented on the surface of a cell or exosome, preferably as a complex with an HLA antigen. Therefore, it is preferable to select peptides that not only induce CTLs but also possess high binding affinity to the HLA antigen. To that end, the peptides can be modified by substitution, insertion, deletion and/or addition of the amino acid residues to yield a modified peptide having improved binding affinity. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. For example, it may be desirable to substitute the second amino acid from the N-terminus with phenylalanine, tyrosine, methionine, or tryptophan, and/or the amino acid at the C-terminus with phenylalanine, leucine, isoleucine, tryptophan, or methionine in order to increase the HLA-A24 binding affinity. Thus, peptides having an amino acid sequence selected from among SEQ ID NOs: 3, 4, 11, 14, 22 and 23 wherein the second amino acid from the N-terminus of the amino acid sequence of the SEQ ID NOs is substituted with phenylalanine, tyrosine, methionine, or tryptophan, and/or wherein the C-terminus of the amino acid sequence of the SEQ ID NOs is substituted with phenylalanine, leucine, isoleucine, tryptophan, or methionine are encompassed by the present invention. Substitutions can be introduced not only at the terminal amino acids but also at the position of potential TCR recognition of peptides. Several studies have demonstrated that amino acid substitutions in a peptide can be equal to or better than the original, for example CAP1, $p53_{(264-272)}$ Her-2/$neu_{(369-377)}$ or $gp100_{(209-217)}$ (Zaremba et al. Cancer Res. 57, 4570-4577, 1997, T. K. Hoffmann et al. J Immunol. (2002) February 1; 168(3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one to two amino acids to the N and/or C-terminus of the described peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce cytotoxic T lymphocytes (CTLs) when presented on antigen-presenting cells. Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radiolabeled with $^{51}$Cr and such, and cytotoxic activity can be calculated from radioactivity released from the target cells. Alternatively, CTL inducibility can be assessed by measuring IFN-gamma produced and released by CTL in the presence of antigen-presenting cells (APCs) that carry immobilized peptides, and visualizing the inhibition zone on the media using anti-IFN-gamma monoclonal antibodies.

As a result of examining the CTL inducibility of the peptides as described above, it was discovered that those having high binding affinity to an HLA antigen did not necessarily have high CTL inducibility. However, of those peptides identified and assessed, nonapeptides or decapeptides having the amino acid sequence selected from among SEQ ID NOs: 3, 4, 11, 14, 22 and 23 were found to exhibit particularly high CTL inducibility as well as high binding affinity to an HLA antigen. Thus, these peptides are exemplified as preferred embodiments of the present invention.

In addition to the above-described modifications, the peptides of the present invention can also be linked to other substances, so long as the resulting linked peptide retains the CTL inducibility of the original peptide. Examples of suitable substances include, for example: peptides, lipids, sugar and sugar chains, acetyl groups, natural and synthetic polymers, etc. The peptides can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept can also be adapted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

The peptides of the present invention are presented on the surface of a cell (e.g. antigen presenting cell) or an exosome as complexes in combination with HLA antigens and then induce CTLs. Therefore, the peptides forming complexes with HLA antigens on the surface of a cell or an exsosomes are also included in the present invention. Such exosomes can be prepared, for example using the methods detailed in Japanese Patent Application Kohyo Publications Nos. Hei 11-510507 and WO99/03499, and can be prepared using APCs obtained from patients who are subject to treatment and/or prevention. The exosomes or cells presenting the peptides of the present invention can be inoculated as vaccines.

The type of HLA antigens contained in the above complexes must match that of the subject requiring treatment and/or prevention. For example, in the Japanese population, HLA-A24, particularly HLA-A2402, is prevalent and therefore would be appropriate for treatment of a Japanese patient. The use of the A24 type that is highly expressed among the Japanese and Caucasian is favorable for obtaining effective results, and subtypes such as A2402 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation.

When using the A24 type HLA antigen for the exosome or cell, the peptides having the amino acid sequence selected from among SEQ ID NO: 3, 4, 11, 14, 22 and 23 are preferably used.

Herein, the peptides of the present invention can also be described as "CDCA1 peptide(s)" or "CDCA1 polypeptide(s)".

III. Preparation of CDCA1 Peptides

The peptides of the invention can be prepared using well known techniques. For example, the peptides can be prepared synthetically, using recombinant DNA technology or chemical synthesis. Peptide of the invention can be synthesized individually or as longer polypeptides composed of two or more peptides. The peptides can be then be isolated, i.e., purified, so as to be substantially free of other naturally occurring host cell proteins and fragments thereof, or any other chemical substances.

A peptide of the present invention can be obtained through chemical synthesis based on the selected amino acid sequence. Examples of conventional peptide synthesis methods that can be adapted for the synthesis include:
(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adopting an in vitro translation system.

IV. Polynucleotides

The present invention also provides a polynucleotide which encodes any of the aforementioned peptides of the present invention. These include polynucleotides derived from the natural occurring CDCA1 gene (GenBank Accession No. NM_145697 (SEQ ID NO: 34)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. Antigen-Presenting Cells (APCs)

The present invention also provides antigen-presenting cells (APCs) that present complexes formed between HLA antigens and the peptides of the present invention on its surface. The APCs that are obtained by contacting the peptides of the present invention, or introducing the nucleotides encoding the peptides of the present invention in an expressible form can be derived from patients who are subject to treatment and/or prevention, and can be administered as vaccines by themselves or in combination with other drugs including the peptides of the present invention, exosomes, or cytotoxic T cells.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, an APC can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. The phrase "inducing APC" includes contacting (stimulating) a cell with the peptides of the present invention, or nucleotides encoding the peptides of the present invention to present complexes formed between HLA antigens and the peptides of the present invention on cell's surface. Alternatively, after introducing the peptides of the present invention to the APCs to allow the APCs to present the peptides, the APCs can be administered to the subject as a vaccine. For example, the ex vivo administration can include steps of:

a: collecting APCs from a first subject,
b: contacting with the APCs of step a, with the peptide and
c: administering the peptide-loaded APCs to a second subject.

The first subject and the second subject may be the same individual, or can be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells, wherein the method comprises the step for admixing or formulating the peptide of the present invention with a pharmaceutically acceptable carrier. Further, the present invention also provides the peptides of the present invention for inducing antigen-presenting cells. The APCs obtained by step (b) can be administered to the subject as a vaccine.

According to an aspect of the present invention, the APCs have a high level of CTL inducibility. In the term of "high level of CTL inducibility", the high level is relative to the level of that by APC contacting with no peptide or peptides which can not induce the CTL. Such APCs having a high level of CTL inducibility can be prepared by a method which includes the step of transferring genes containing polynucleotides that encode the peptides of the present invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VI. Cytotoxic T Cells

A cytotoxic T cell induced against any of the peptides of the present invention strengthens the immune response targeting cancer cells in vivo and thus can be used as vaccines, in a fashion similar to the peptides per se. Thus, the present invention also provides isolated cytotoxic T cells that are specifically induced or activated by any of the present peptides.

Such cytotoxic T cells can be obtained by (1) administering the peptides of the present invention to a subject, collecting cytotoxic T cells from the subject or (2) contacting (stimulating) subject-derived APCs and CD8-positive cells, or peripheral blood mononuclear leukocytes in vitro with the peptides of the present invention and then isolating cytotoxic T cells.

The cytotoxic T cells, which have been induced by stimulation with APCs that present the peptides of the present invention, can be derived from patients who are subject to treatment and/or prevention, and can be administered by themselves or in combination with other drugs including the peptides of this invention or exosomes for the purpose of regulating effects. The obtained cytotoxic T cells act specifically against target cells presenting the peptides of the present invention, for example, the same peptides used for induction. The target cells can be cells that endogenously express CDCA1, or cells that are transfected with the CDCA1 gene; and cells that present a peptide of the present invention on the cell surface due to stimulation by the peptide can also serve as targets of activated CTL attack.

VII. T Cell Receptor (TCR)

The present invention also provides a composition containing nucleic acids encoding polypeptides that are capable of forming a subunit of a T cell receptor (TCR), and methods of using the same. The TCR subunits have the ability to form TCRs that confer specificity to T cells against tumor cells presenting CDCA1. By using the known methods in the art, the nucleic acids of alpha- and beta-chains as the TCR subunits of the CTL induced with one or more peptides of the present invention can be identified (WO2007/032255 and Morgan et al., J Immunol, 171, 3288 (2003)). The derivative TCRs can bind target cells displaying the CDCA1 peptide with high avidity, and optionally mediate efficient killing of target cells presenting the CDCA1 peptide in vivo and in vitro.

The nucleic acids encoding the TCR subunits can be incorporated into suitable vectors e.g. retroviral vectors. These vectors are well known in the art. The nucleic acids or the vectors containing them usefully can be transferred into a T cell, for example, a T cell from a patient. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides that bind to the CDCA1 peptide e.g. SEQ ID NOs: 3, 4, 11, 14, 22 and 23 in the context of HLA-A24. The transduced CTLs are capable of homing to cancer cells in vivo, and can be expanded by well known culturing methods in vitro (e.g., Kawakami et al., J Immunol., 142, 3452-3461 (1989)). The T cells of the invention can be used to form an immunogenic composition useful in treating or the prevention of cancer in a patient in need of therapy or protection (WO2006/031221).

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

Treating and/or for the prophylaxis of cancer or, and/or the prevention of postoperative recurrence thereof includes any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

VIII. Pharmaceutical Agents or Compositions

Since CDCA1 expression is specifically elevated in several cancer types, including breast cancer, bladder cancer, esophageal cancer, small cell lung cancer (SCLC) and non-small cell lung cancer (NSCLC) as compared with normal tissue (Cancer Res 2006 Nov. 1; 66(21):10339-48, WO2005/028676, WO2005/089735, WO2006/085684, WO2007/013665, WO2007/013671), the peptides of the present invention or polynucleotides encoding the peptides can be used for the treatment and/or prophylaxis of cancer or tumor, and/or for the prevention of postoperative recurrence thereof. Thus, the present invention provides a pharmaceutical agent or a composition for treating and/or for the prophylaxis of cancer or tumor, and/or prevention of postoperative recurrence thereof, which comprises one or more of the peptides of the present invention, or polynucleotides encoding the peptides as an active ingredient. Alternatively, the present peptides can be expressed on the surface of any of the foregoing exosomes or cells, such as APCs for the use as pharmaceutical agents or compositions. In addition, the aforementioned cytotoxic T cells which target any of the peptides of the invention can also be used as the active ingredient of the present pharmaceutical agents or compositions.

In another embodiment, the present invention also provides the use of an active ingredient selected from among:
(a) a peptide of the present invention,
(b) a nucleic acid encoding such a peptide as disclosed herein in an expressible form,
(c) an APC or an exosome presenting a peptide of the present invention on its
surface, and
(d) a cytotoxic T cell of the present invention
in manufacturing a pharmaceutical composition or agent for treating cancer or tumor.

Alternatively, the present invention further provides an active ingredient selected from among:
(a) a peptide of the present invention,
(b) a nucleic acid encoding such a peptide as disclosed herein in an expressible form, (c) an APC or an exosome presenting a peptide of the present invention on its surface, and
(d) a cytotoxic T cells of the present invention for use in for treating cancer or tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
(a) a peptide of the present invention,
(b) a nucleic acid encoding such a peptide as disclosed herein in an expressible form,
(c) an APC or an exosome presenting a peptide of the present invention on its surface, and
(d) a cytotoxic T cells of the present invention
as active ingredients.

In another embodiment, the present invention also provides a method or process for manufacturing a pharmaceutical composition or agent for treating cancer or tumor, wherein the method or process includes the step of admixing an active ingredient with a pharmaceutically or physiologically acceptable carrier, wherein the active ingredient is selected from among:
(a) a peptide of the present invention,
(b) a nucleic acid encoding such a peptide as disclosed herein in an expressible form,
(c) an APC or an exosome presenting a peptide of the present invention on its surface, and
(d) a cytotoxic T cells of the present invention.

Alternatively, the pharmaceutical composition or agent of the present invention may be used for either or both the prophylaxis of cancer or tumor and prevention of postoperative recurrence thereof.

The present pharmaceutical agents or compositions find use as a vaccine. In the context of the present invention, the phrase "vaccine" (also referred to as an immunogenic composition) refers to a substance that has the function to induce anti-tumor immunity upon inoculation into animals.

The pharmaceutical agents or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, polypeptides having an amino acid sequence selected from among SEQ ID NO: 3, 4, 11, 14, 22 and 23 have been found to be HLA-A24 restricted epitope peptides or candidates that can induce potent and specific immune response. Therefore, the present pharmaceutical agents which include any of these polypeptides having the amino acid sequences of SEQ ID NOs: 3, 4, 11, 14, 22 and 23 are particularly suited for the administration to subjects whose HLA antigen is HLA-A24. The same applies to pharmaceutical agents or compositions which contain polynucleotides encoding any of these polypeptides.

Cancers or tumors to be treated by the pharmaceutical agents or compositions of the present invention are not limited and include all kinds of cancers or tumors wherein CDCA1 is involved, including for example, breast cancer, bladder cancer, esophageal cancer, small cell lung cancer (SCLC) and non-small cell lung cancer (NSCLC).

The present pharmaceutical agents or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention can optionally include other therapeutic substances as an active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents or compositions of the present invention can include other agents conventional in the art having regard to the type of formulation in question.

In one embodiment of the present invention, the present pharmaceutical agents or compositions can be included in articles of manufacture and kits containing materials useful for treating the pathological conditions of the disease to be treated, e.g, cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptide of the present invention can be administered directly as a pharmaceutical agent or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared in a combination, composed of two or more of peptides of the present invention to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different.

By administering the peptides of the present invention, the peptides are presented at a high density by the HLA antigens on APCs, then CTLs that specifically react toward the complex formed between the displayed peptide and the HLA antigen are induced. Alternatively, APCs that present any of the peptides of the present invention on their cell surface, which may be obtained by stimulating APCs (e.g., DCs) derived from a subject with the peptides of the present invention, may be administered to the subject, and as a result, CTLs are induced in the subject and aggressiveness towards the cancer cells can be increased.

The pharmaceutical agents or compositions for the treatment and/or prevention of cancer or tumor, which include a peptide of the present invention as the active ingredient, can also include an adjuvant known to effectively establish cellular immunity. Alternatively, the pharmaceutical agents or compositions can be administered with other active ingredients or can be administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, and the like.

Furthermore, liposome formulations, granular formulations in which the peptide is bound to few-micrometers diameter beads, and formulations in which a lipid is bound to the peptide may be conveniently used.

In some embodiments, the pharmaceutical agents or compositions of the present invention may further include a component which primes CTLs. Lipids have been identified as agents capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinlyseryl-serine (P3CSS) can be used to prime CTLs when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents or Compositions Containing Polynucleotides as the Active Ingredient The pharmaceutical agents or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, N Y, 1993; and Krieger, Gene Transfer and Expression, A Laboratory Manual, Stockton Press, N Y, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

IX. Methods Using the Peptides, Exosomes, APCs and CTLs

The peptides of the present invention and polynucleotides encoding such peptides can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also be used for inducing APCs as discussed below.

(1) Method of Inducing Antigen-Presenting Cells (APCs)

The present invention provides methods of inducing APCs using the peptides of the present invention or polynucleotides encoding the peptides. The induction of APCs can be performed as described above in section "VI. Antigen-presenting cells". The present invention also provides a method for inducing APCs having a high level of CTL inducibility, the induction of which has been also mentioned under the item of "VI. Antigen-presenting cells", supra.

(2) Method of Inducing CTLs

Furthermore, the present invention provides methods for inducing CTLs using the peptides of the present invention, polynucleotides encoding the peptides, exosomes or APCs presenting the peptides. The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs comprise at least one step selected from the group consisting of:
a: contacting a CD8-positive T cell with an antigen-presenting cell and/or an exosome that presents on its surface a complex of an HLA antigen and the peptide of the present invention, and
b: introducing a polynucleotide encoding a polypeptide that is capable of forming a TCR subunit recognizing a complex of the peptide of the present invention and an HLA antigen into a CD8 positive T cell.

When the peptides of the present invention are administered to a subject, CTLs are induced in the body of the subject, and the strength of the immune response targeting the cancer cells is enhanced. Alternatively, the peptides and polynucleotides encoding the peptides can be used for an ex vivo therapeutic method, in which subject-derived APCs and CD8-positive cells, or peripheral blood mononuclear leukocytes are contacted (stimulated) with the peptides of the present invention in vitro, and after inducing CTLs, the activated CTL cells are returned to the subject. For example, the method can include the steps of:

a: collecting APCs from subject,
b: contacting with the APCs of step a, with the peptide,
c: mixing the APCs of step b with $CD^{8+}$ T cells, and co-culturing for inducing CTLs: and
d: collecting $CD^{8+}$ T cells from the co-culture of step c.

Alternatively, according to the present invention, use of the peptides of the present invention for manufacturing a pharmaceutical agent or composition inducing CTLs is provided. In addition, the present invention provides a method or process for manufacturing a pharmaceutical agent or composition inducing CTLs, wherein the method comprises the step for admixing or formulating the peptide of the present invention with a pharmaceutically acceptable carrier. Further, the present invention also provides the peptide of the present invention for inducing CTLs.

The $CD^{8+}$ T cells having cytotoxic activity obtained by step d can be administered to the subject as a vaccine. The APCs to be mixed with the $CD^{8+}$ T cells in above step c can also be prepared by transferring genes coding for the present peptides into the APCs as detailed above in section "VI. Antigen-presenting cells"; but are not limited thereto. Accordingly, any APCs or exosomes which effectively presents the present peptides to the T cells can be used for the present method.

The following examples are presented to illustrate the present invention and to assist one of ordinary skill in making and using the same. The examples are not intended in any way to otherwise limit the scope of the invention.

Examples

Materials and Methods

Cell Lines

A24 lymphoblastoid cell line (A24LCL) cells were established by transformation with Epstein-bar virus into HLA-A24 positive human B lymphocyte.

Candidate Selection of Peptides Derived from CDCA1

9-mer and 10-mer peptides derived from CDCA1 that bind to HLA-A*2402 were predicted using binding prediction software "BIMAS" (www.bimas.cit.nih.gov/molbio/hla_bind), which algorithms had been described by Parker K C et al. (J Immunol 1994, 152(1): 163-75) and Kuzushima K et al. (Blood 2001, 98(6): 1872-81). These peptides were synthesized by American Peptide Company Inc. (Sunnyvale, Calif.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System)

in AIM-V Medium (Invitrogen) containing 2% heat-inactivated autologous serum (AS). After 7 days of culture, the cytokine-induced DCs were pulsed with 20 micro g/ml of each of the synthesized peptides in the presence of 3 micro g/ml of beta 2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by Mitomycin C (MMC) (30 micro g/ml for 30 min) and mixed at a 1:20 ratio with autologous CD8+ T cells, obtained by positive selection with CD8 Positive Isolation Kit (Dynal). These cultures were set up in 48-well plates (Corning); each well contained $1.5\times10^4$ peptide-pulsed DCs, $3\times10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed A24LCL cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5\times10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1\times10^4$ cells/well of 2 kinds of human B-lymphoblastoid cell lines, 30 ng/ml of anti-CD3 antibody, and 125 U/ml of IL-2 in a total of 150 micro l/well of AIM-V Medium containing 5% AS. 50 micro l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed A24LCL ($1\times10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A24

The cDNA encoding an open reading frame of target genes or HLA-A24 was amplified by PCR. The PCR-amplified product was cloned into pCAGGS vector. The plasmids were transfected into COST, which is the target genes and HLA-A24-null cell line, using lipofectamine 2000 (Invitrogen) according to the manufacturer's recommended procedures. After 2 days from transfection, the transfected cells were harvested with versene (Invitrogen) and used as the target cells ($5\times10^4$ cells/well) for CTL activity assay.

Results

Prediction of HLA-A24 Binding Peptides Derived from CDCA1

Table 1 shows the HLA-A*2402 binding peptides of CDCA1 in order of highest binding affinity. A total of 40 peptides having potential HLA-A24 binding ability were selected and examined to determine the epitope peptides.

TABLE 1

| HLA-A24 binding peptides derived from CDCA1 | | | |
|---|---|---|---|
| Start position | Amino acid sequence | Binding score | SEQ ID NO. |
| 36 | LYPNPKPEVL | 300 | 1 |
| 74 | MYPHLMEGFL | 300 | 2 |
| 119 | RFLSGIINFI | 25.2 | 3 |
| 335 | KTEENSFKRL | 17.28 | 4 |
| 432 | KYHDGIEKAA | 16.8 | 5 |
| 181 | KQLSDGIQEL | 15.84 | 6 |
| 64 | FYMMPVNSEV | 11.55 | 7 |
| 295 | LYQKKIQDLS | 10.5 | 8 |
| 309 | KLASILKESL | 9.6 | 9 |
| 146 | KSSADKMQQL | 9.6 | 10 |
| 48 | IYMRALQIVY | 9 | 11 |
| 185 | DGIQELQQSL | 8.64 | 12 |
| 231 | VSLKEIQESL | 8.4 | 13 |
| 5 | SFPRYNVAEI | 8.25 | 14 |
| 394 | INQEIQKIKL | 7.92 | 15 |
| 322 | DQIESDESEL | 7.92 | 16 |
| 87 | NLVTHLDSFL | 7.2 | 17 |
| 368 | QYKRTVIEDC | 7 | 18 |
| 295 | LYQKKIQDL | 360 | 19 |
| 278 | IYGDSVDCL | 240 | 20 |
| 74 | MYPHLMEGF | 180 | 21 |
| 8 | RYNVAEIVI | 150 | 22 |
| 56 | VYGIRLEHF | 100 | 23 |
| 422 | IFLNLKTAL | 36 | 24 |
| 119 | RFLSGIINF | 30 | 25 |

TABLE 1-continued

HLA-A24 binding peptides derived from CDCA1

| Start position | Amino acid sequence | Binding score | SEQ ID NO. |
|---|---|---|---|
| 144 | QYKSSADKM | 27.5 | 26 |
| 418 | KSQEIFLNL | 24.192 | 27 |
| 197 | DFHQKTIVL | 20 | 28 |
| 275 | KYEIYGDSV | 15 | 29 |
| 432 | KYHDGIEKA | 13.2 | 30 |
| 387 | VYERVTTIN | 10.5 | 31 |
| 186 | GIQELQQSL | 10.368 | 32 |
| 48 | IYMRALQIV | 9 | 33 |

Start position indicates the number of amino acid residue from the N-terminal of CDCA1.
Binding score is derived from "BIMAS".

CTL Induction with the Predicted Peptides from CDCA1 Restricted with HLA-A*2402 and Establishment for CTL Lines Stimulated with CDCA1 Derived Peptides CTLs for those peptides derived from CDCA1 were generated according to the protocols as described in "Materials and Methods". Peptide specific CTL activity was determined by IFN-gamma ELISPOT assay (FIG. 1a-f). It showed that CDCA1-A24-10-119 (SEQ ID NO: 3), CDCA1-A24-10-335 (SEQ ID NO: 4), CDCA1-A24-10-48 (SEQ ID NO: 11), CDCA1-A24-10-5 (SEQ ID NO: 14), CDCA1-A24-9-8 (SEQ ID NO: 22) and CDCA1-A24-9-56 (SEQ ID NO: 23) demonstrated potent IFN-gamma production as compared to the control wells. Furthermore, the cells in the positive well number #8 stimulated with CDCA1-A24-10-119 (SEQ ID NO: 3), #1 with CDCA1-A24-10-335 (SEQ ID NO: 4), #1 with CDCA1-A24-10-48 (SEQ ID NO: 11), #4 with CDCA1-A24-10-5 (SEQ ID NO: 14), #2 with CDCA1-A24-9-8 (SEQ ID NO: 22) and #2 with CDCA1-A24-9-56 (SEQ ID NO: 23) were expanded and established CTL lines. CTL activity of those CTL lines was determined by IFN-gamma ELISA assay (FIG. 2a-f). It showed that all CTL lines demonstrated potent IFN-gamma production against the target cells pulsed with corresponding peptide as compared to target cells without peptide pulse. On the other hand, no CTL lines could be established by stimulation with other peptides, despite the peptides had possible binding activity with HLA-A*2402. For example, typical negative data of CTL response stimulated with CDCA1-A24-10-74 (SEQ ID NO: 2) was shown in FIG. 1g and FIG. 2g. The results herein indicate that six peptides derived from CDCA1 have ability to induce potent CTL lines.

Establishment of CTL Clones Against CDCA1 Specific Peptides

CTL clones were established by limiting dilution from CTL lines as described in "Materials and Methods", and IFN-gamma production from CTL clones against target cells pulsed peptide were determined by IFN-gamma ELISA assay. Potent IFN-gamma productions were determined from CTL clones stimulated with SEQ ID NO: 23 in FIG. 3.

Specific CTL Activity Against Target Cells Exogenously Expressing CDCA1 and HLA-A*2402

The established CTL lines raised against these peptides were examined for their ability to recognize target cells that exogenously express CDCA1 and HLA-A*2402 molecule. Specific CTL activity against COS7 cells which transfected with both the full length of CDCA1 and HLA-A*2402 molecule gene (a specific model for the target cells that exogenously express CDCA1 and HLA-A*2402 gene) was tested using the CTL lines raised by corresponding peptide as the effecter cells. COS7 cells transfected with either full length of CDCA1 genes or HLA-A*2402 were prepared as control. In FIG. 4, the CTLs stimulated with SEQ ID NO: 23 showed potent CTL activity against COS7 cells expressing both CDCA1 and HLA-A*2402. On the other hand, no significant specific CTL activity was detected against the controls. Thus, these data clearly demonstrate that the peptide having the amino acid sequence of SEQ ID NO: 23 is naturally presented on the target cells with HLA-A*2402 molecule and is recognized by the CTLs. The results indicate that this peptide derived from CDCA1 may be applicable for cancer immunotherapy, particularly as a cancer vaccine for patients with CDCA1 expressing tumors.

Homology Analysis of Antigen Peptides

The CTLs stimulated with CDCA1-A24-10-119 (SEQ ID NO: 3), CDCA1-A24-10-335 (SEQ ID NO: 4), CDCA1-A24-10-48 (SEQ ID NO: 11), CDCA1-A24-10-5 (SEQ ID NO: 14), CDCA1-A24-9-8 (SEQ ID NO: 22) and CDCA1-A24-9-56 (SEQ ID NO: 23) showed significant and specific CTL activity. This result may be due to the fact that the sequences of CDCA1-A24-10-119 (SEQ ID NO: 3), CDCA1-A24-10-335 (SEQ ID NO: 4), CDCA1-A24-10-48 (SEQ ID NO: 11), CDCA1-A24-10-5 (SEQ ID NO: 14), CDCA1-A24-9-8 (SEQ ID NO: 22) and CDCA1-A24-9-56 (SEQ ID NO: 23) are homologous to peptides derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequences with significant homology. The results of homology analyses indicate that the sequences of CDCA1-A24-10-119 (SEQ ID NO: 3), CDCA1-A24-10-335 (SEQ ID NO: 4), CDCA1-A24-10-48 (SEQ ID NO: 11), CDCA1-A24-10-5 (SEQ ID NO: 14), CDCA1-A24-9-8 (SEQ ID NO: 22) and CDCA1-A24-9-56 (SEQ ID NO: 23) are unique and thus, there is little possibility that these molecules raise unintended immunologic responses to some unrelated molecules.

In conclusion, novel HLA-A24 epitope peptides derived from CDCA1 were identified and demonstrated to be applicable for cancer immunotherapy.

INDUSTRIAL APPLICABILITY

The present invention describes new TAAs, particularly those derived from CDCA1 which induce potent and specific anti-tumor immune responses and have applicability to a wide array of cancer types. Such TAAs warrant further development as peptide vaccines against diseases associated with CDCA1, e.g. cancers, more particularly, testicular tumor, pancreatic cancer, bladder cancer, non-small cell lung cancer, small cell lung cancer and esophageal cancer.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. A method of inducing an immune response against a cancer expressing CDCA1 in a subject whose HLA is HLA-A*2402, said method comprising the step of administering an isolated peptide consisting of the amino acid sequence of SEQ ID NO: 23 to said subject.

* * * * *